United States Patent [19]

Ham et al.

[11] Patent Number: 4,824,533
[45] Date of Patent: Apr. 25, 1989

[54] PROCESS FOR PREPARING TETRAHALOPYRIDINE

[75] Inventors: George E. Ham; Robert D. Spradling; John M. McIntyre, all of Lake Jackson, Tex.

[73] Assignee: The Dow Chemical Company, Midland, Mich.

[21] Appl. No.: 899,267

[22] Filed: Aug. 22, 1986

[51] Int. Cl.$^4$ .............................................. C07D 213/61
[52] U.S. Cl. .............................. 204/73 R; 204/59 R; 204/59 F; 204/62; 204/72
[58] Field of Search ............... 204/73 R, 72, 62, 59 R, 204/59 F

[56] References Cited

U.S. PATENT DOCUMENTS

| | | | |
|---|---|---|---|
| 3,677,916 | 7/1972 | Seiber | 204/59 R |
| 3,694,332 | 9/1972 | Parker | 204/73 R |
| 4,592,810 | 6/1986 | Bon et al. | 204/73 R |

Primary Examiner—Arthur P. Demers
Attorney, Agent, or Firm—A. Triantaphyllis; Kurt S. Myers

[57] ABSTRACT

Symmetrical or 2,3,5,6-tetrahalopyridine is prepared from pentahalopyridine in an electrolytic cell by forming an organic solvent-free emulsion of pentahalopyridine and tetrahalopyridine and by electrolyzing the emulsion.

25 Claims, 1 Drawing Sheet

PROCESS FOR PREPARING TETRAHALOPYRIDINE

TECHNICAL FIELD

The present invention relates to the preparation of chloro substituted pyridines and more particularly, to the preparation of 2,3,5,6-tetrahalopyridines. Still more particularly, the present invention relates to the preparation of 2,3,5,6-tetrahalopyridines from pentahalopyridine by electrolysis in the absence of an organic solvent.

BACKGROUND OF THE INVENTION 2,3,5,6 or symmetrical tetrachloropyridine is used for the preparation of herbicides and pesticides. Numerous processes have been employed in the past for the preparation of 2,3,5,6-tetrachloropyridine. Several processes that utilize non-electrolytic methods are disclosed in U.S. Pat. Nos. 3,186,994; 3,538,100; 3,993,654; 4,127,575; 4,256,894; 4,259,495; 4,281,135; 4,321,389; 4,322,538; and 4,327,216. Among those methods, the methods disclosed in U.S. Pat. Nos. 3,993,654; 4,259,495; 4,321,389; and 4,322,538 are methods wherein 2,3,5,6-tetrachloropyridine is produced from pentachloropyridine.

U.S. Pat. No. 3,993,654 discloses a process for preparing 2,3,5,6-tetrachloropyridine by heating pentachloropyridine in an aqueous medium under pressure, with agitation, in the presence of zinc and hydrogen chloride. U.S. Pat. No. 4,259,495 discloses a process for the preparation of 2,3,5,6-tetrachloropyridine by dechlorinating pentachloropyridine in an ester solvent, in the presence of an ammonium salt of an inorganic or an organic acid. U.S. Pat. No. 4,321,389 discloses a process for the production of 2,3,5,6-tetrachloropyridine by transhalogenating pentachloropyridine by a bromide salt in a polar, aprotic solvent at a temperature from about 100° C. to about 140° C., followed by selectively debrominating with hydrogen, in the presence of a noble metal catalyst and an acid acceptor. U.S. Pat. No. 4,322,538 discloses a process for producing 2,3,5,6-tetrachloropyridine by reacting pentachloropyridine with iodide ions and a proton donor and a polar, aprotic solvent at a temperature from about 100° C. to 200° C.

Some of the disadvantages of the aforementioned processes utilizing pentachloropyridine as the starting material to produce 2,3,5,6-tetrachloropyridine include the disposal problems associated therewith, i.e., zinc chloride produced in the method disclosed in the U.S. Pat. No. 3,993,654; the need for separating the products from the solvents in the processes where such solvents are used; and the costs associated with the use of catalysts and the use of solvents.

In addition to the aforementioned non-electrolytic processes used for the preparation of 2,3,5,6-tetrachloropyridine from pentachloropyridine, and electrolytic process is disclosed in U.S. Pat. No. 3,694,332, wherein a pentahalopyridine is electrolytically reduced to prepare a 2,3,5,6-tetrahalopyridine. The starting halogenated pyridine is dissolved in a suitable solvent containing an electrolyte, the solution is added to an electrolytic cell and current is passed through the cell until the desired degree of reduction is obtained. The cell utilized is a conventional one with or without a diaphragm. Preferred electrolytes are neutral or acidic salts. Several solvents could be employed depending on the reaction being considered.

Some of the disadvantages of the method disclosed in the U.S. Pat. No. 3,694,332 arise because of the use of the solvent. Those disadvantages include the reduction of the concentration of the electrolyte whereby the electrochemical operation of the reaction is hampered; the need for separating the product from the solvent following the electrolytic reaction; the complication of the operation; the increase in energy consumption; and increase in the potential of environmental pollution.

The present invention discloses an electrolytic reaction wherein pentahalopyridine is reduced to 2,3,5,6-tetrahalopyridine without utilizing an organic solvent, whereby all the disadvantages associated with the use of such solvent in U.S. Pat. No. 3,694,332 are eliminated.

These and other advantages of the present invention will become apparent from the following description.

SUMMARY OF THE INVENTION 2,3,5,6-tetrahalopyridine is manufactured by the electrolytic reduction of pentahalopyridine in the liquid phase without utilizing an organic solvent. The reaction is carried out in a conventional electrolytic cell utilizing an aqueous electrolyte.

BRIEF DESCRIPTION OF THE DRAWINGS

For a detailed description of the invention, reference will now be made to the accompanying drawing, wherein.

DETAILED DESCRIPTION OF THE INVENTION

Figure 1:
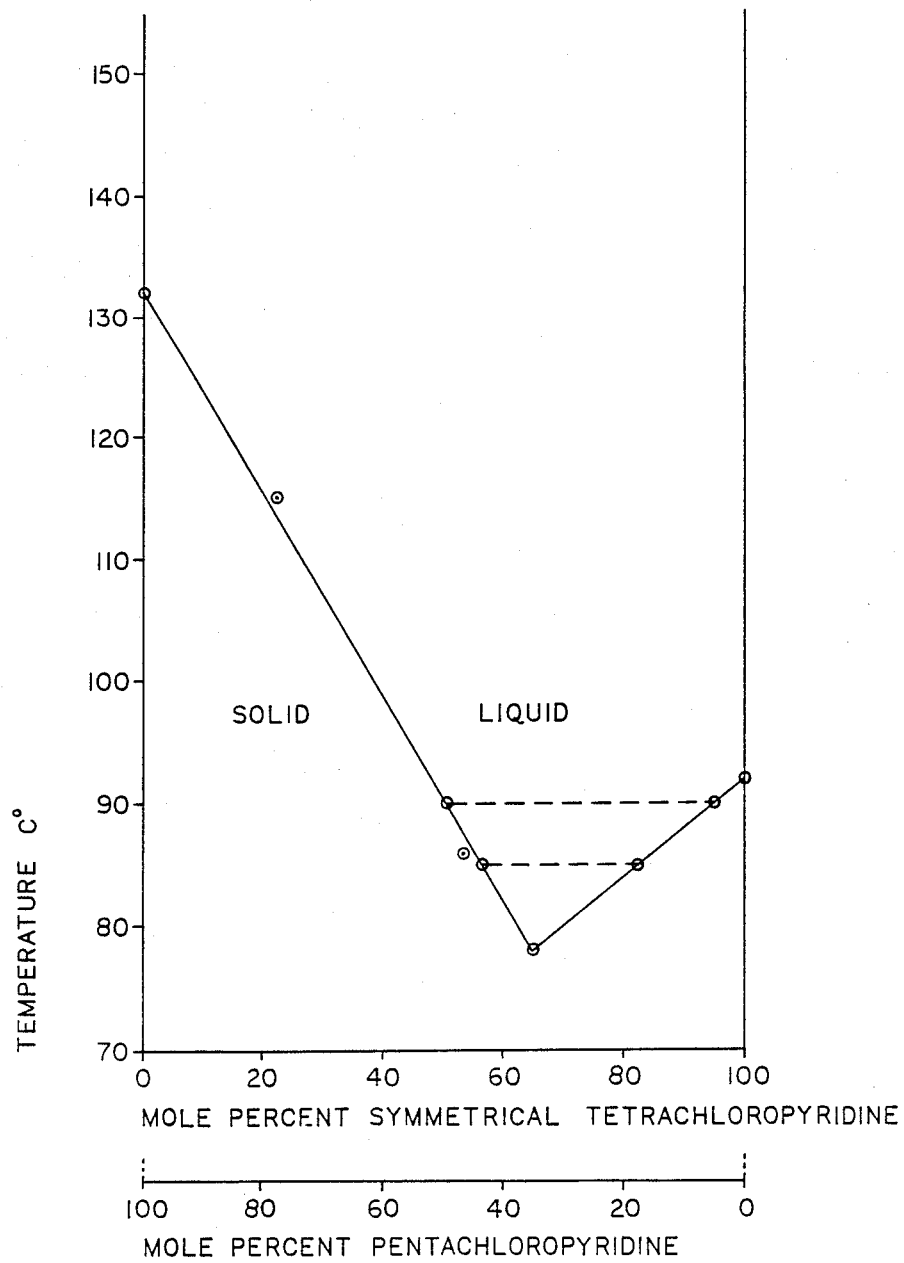
FIG. 1 is a graph showing the melting points of pentachloropyridine/symmetrical tetrachloropyridine mixture versus the composition of the mixture.

According to the present invention, symmetrical tetrahalopyridine is produced in an electrolytic cell by electrolyzing a pentahalopyridine in the absence of an organic solvent. A liquid mixture of pentahalopyridine and tetrahalopyridine is dispersed or emulsified in an aqueous electrolyte. The emulsion is subjected to electrolysis and the pentahalopyridine is converted to tetrahalopyridine by the following cathode reaction:

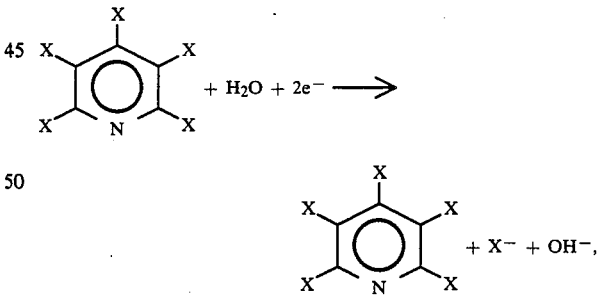

where X is a halogen. The electrolytic cell effluent contains an organic phase and an aqueous electrolyte phase. The two phases are easily separated by conventional means to obtain an organic product and to recover the electrolyte for further use in the electrolytic cell. Any pentahalopyridine that has not been converted is separated from the organic product by conventional means for use as feed to the electrolytic cell.

In the absence of an organic solvent, the organic material is maintained in a liquid phase by carrying out the reaction at a temperature above the melting point temperature of the organic mixture. Furthermore, because the melting point temperature of the mixture is a function of the composition of the mixture and because the composition of the mixture changes during the reaction as pentahalopyridine is converted to 2,3,5,6-tetrahalopyridine, the reaction is carried out at a temperature that is higher than the melting point temperatures of all the mixture compositions encountered during the reaction.

For purposes of illustration, reference is now made to FIG. 1 showing the melting points of a pentachloropyridine/symmetrical tetrachloropyridine mixture versus the mole composition of the mixture. It should be understood that the melting points shown in FIG. 1 represent the temperature at which the melting commences. The melting point temperature of pure tetrahalopyridine is about 132° C. When a mixture is formed by adding symmetrical tetrachloropyridine the melting point temperature of the mixture decreases to about 78° C. as the amount of symmetrical tetrachloropyridine in the mixture increases from zero percent to about 64 mole percent. At that point the trend is reversed and the melting point temperature of the mixture increases from 78° C. to about 92° C. as the amount of symmetrical tetrachloropyridine in the mixture increases from about 64 mole percent to one hundred percent. It is apparent from the aforementioned FIG. 1 that, if the temperature of the organic mixture is above 132° C., the mixture is in the liquid phase, regardless of the composition thereof. Similarly, if the temperature of the mixture is below 78° C., at least a portion of the mixture is in the solid phase, regardless of its composition. Furthermore, it is apparent from FIG. 1 that, if the temperature of the mixture is between 78° C. and 132° C., its composition should stay within a certain range to prevent solidification of that mixture and to maintain the mixture in the liquid phase. If, for example, the temperature of the mixture is 85° C., the amount of symmetrical tetrachloropyridine in the mixture should be not less than about 57 mole percent and not more than about 82 mole percent to maintain the liquid phase. Accordingly, at that temperature, the pentahalopyridine conversion could not exceed 59 percent.

The melting point temperatures of other pentahalopyridine/symmetrical tetrahalopyridine mixtures wherein the halogen is other than chlorine are also a function of the composition of such mixtures. The correlation between the two parameters exhibit characteristics that are similar to the characteristics of the correlation between the melting point temperature and mixture composition of the chloropyridines referred to hereinabove. The actual values, however, are different, due to the presence of a different halogen.

While it is apparent from FIG. 1 that at higher temperatures the electrolysis can be carried out starting from one-hundred percent pentahalopyridine or that the entire pentahalopyridine can be converted, it is preferred to carry out the electrolysis reaction at lower temperatures to avoid the formation of undesirable by-products in the electrolytic reaction and to avoid carrying out the reaction at high pressures. Therefore, one should choose the lowest temperature for a desirable conversion. In the case, for example, of the pentachloropyridine conversion to symmetrical tetrachloropyridine, it is preferred to carry out the reaction at a temperature in the range from 85° C. to 90° C. with corressponding maximum conversions ranging from 59 to 89 percent. Similarly, in the case of the other halogenated pyridines, one skilled in the art may choose the appropriate temperature to achieve the required conversion while preventing solidification of the organic mixture and formation of undesirable by-products.

The pressure conditions of the reaction depend on the temperature conditions thereof. If, for example, the reaction temperature is less than 100° C., the reaction may be conveniently practiced at a pressure that is equal to or slightly above atmospheric pressure. If, however, the reaction temperature is higher than 100° C., the reaction should and could be carried out at higher pressures to avoid vaporization of the water that is present in the aqueous electrolyte.

In practicing the invention, the design of the electrolytic cell is not critical. Conventional electrolytic cells that are well-known in the art, having an anode and a cathode, may be readily employed. Furthermore, the invention may be practiced in an electrolytic cell with or without a cell diaphragm, such as an ion exchange membrane. Preferred cathodes include those made out of lead, silver, mercury, copper, magnetite ($Fe_3O_4$), tin, or zinc with copper or silver being especially preferred. As regards the anode, any chemically inert material such as titanium coated with ruthenium or iridium oxide, magnetite, stainless steel, lead, or platinum may be used. It is preferred, however, to utilize titanium anodes coated with ruthenium oxide because they do not degrade during electrolysis and because of the cost and availability of the material. The anode and the cathode are electrically connected to a positive and negative side of a direct current source, respectively. An electric potential that is sufficient to promote the electrolytic reactions of the present invention is applied across the positive and negative sides of the current source.

While a wide range of electric potentials and current densities may be utilized in the electrolytic cell to practice the invention, it is preferred to remain within certain limits wherein the formation of undesirable by-products is minimized and the reaction rate is sufficient to produce the required amount of product. Accordingly, the electric potential may preferably range from about 2 to 5 Volts and most preferably from 2 to 3 Volts. Similarly, the current density may preferably range from about 0.01 to 2.0 Amps/$In^2$ of electrode with 0.4 to 0.6 Amps/$In^2$ being especially preferred.

The invention may be conveniently practiced by maintaining the current density constant for an extended period of time or by periodically adjusting such current density within the aforementioned ranges. A charged electrode, however, tends to adsorb the organic reactants and products present in the cell, thereby causing the electrode to be covered with slowly desorbing product and the current efficiency of the reaction to decrease. The current efficiency of the reaction may be increased, however, by operating the electrolytic cell in a pulsed current mode. In that mode, electrical current is pulsed to the electrolytic cell by turning the power supply on and off or by varying the voltage. When the current of the cell is turned off or reduced the electrodes are de-energized and the adsorbed product is desorbed. When the current is turned on or increased again, the re-energized electrode that is substantially free of product adsorbs new reactant and the efficiency of the reaction is increased.

The pulse rates may be optimized for the particular reaction and the operating conditions thereof. In the case of the pentachloropyridine to symmetrical tetrachloropyridine reaction, for example, the reaction may be conveniently practiced by operating with a current density of 0.25 Amps/$In^2$ for one minute and by turning off the power unit for 0.25 minutes, etc. Accordingly, other pulsed modes may be used depending on the individual requirements and reaction conditions.

A large number of electrolytes may be used to practice the present invention. It is preferred, however, that electrolytes that are strong bases be avoided because they may be detrimental to the progress of the reaction due to their tendency to result in substitutional reactions with the halogens. Specific electrolytes that may be used include sodium chloride, sodium zincate, sodium toluenesulphonate, sodium acetate, ammonium-toluene sulphonate, ammonium chloride, ammonium fluoride, and tetramethylammonium chloride. Especially preferred is the use of salts of acetic, phosphoric, formic or carbonic acid. The concentration of the electrolyte may vary as different reactant/product concentrations, electrolytes, current densities and electric potentials are employed.

The ratio of the electrolyte to organic reactants and products present in the cell may vary as there are other variables influencing the effect of such ratio on the reaction. It is, however, essential that the weight ratio be between four (4) and eight (8) to obtain optimum results.

The choice of an emulsifier used to practice the reaction is not critical and any emulsifier that would be inert to the reaction could be used. Such emulsifiers include ammonium salt of sulfated dodecylphenoxy poly-(ethyleneoxy) ethanol and other anionic emulsifiers.

The reaction may be carried in a batch or a continuous mode, the latter being preferred. If the batch mode is used, it is preferred to utilize stirring means to maintain the homogenuity of the emulsion.

The life of the electrodes may be increased and other benefits may be obtained if the reaction is carried out at a pH between 6.5 and 9.0. The pH is maintained within the aforementioned range by adding appropriate amounts of suitable agents.

The following examples further illustrate the invention but are not to be construed as limitations on the scope of the process contemplated herein.

EXAMPLE 1

An electrolytic cell was constructed by fitting a fifty (50) milliliter beaker with one-inch by three-inch electrodes. The cathode was made out of lead and the anode of lead-antimony (Pb-Sb). The electrode leads were welded through the sides of the beaker. A ground-glass standard tapered fitting was placed at the top of the beaker. The male portion thereof was connected to a tube leading to a perchloroethylene scrubber. The beaker was placed in a water bath on a magnetic steering hot plate that provided the heat required to maintain the temperature of the water bath between 90° and 95° C. A stirring bar, coated with a material known by the trademark "Teflon", was placed in the beaker and was driven by the magnetic stirring hot plate to provide agitation for the contents of the beaker. A potentionstat-galvanostat, coupled with an integrator with the capability of supplying either constant current or voltage, provided power. The cell voltage was monitored by a multimeter.

Equal amounts of pentachloropyridine and symmetrical tetrachloropyridine were placed in a 250-milliliter beaker and a homogeneous melt was obtained by warming the contents thereof slowly while stirring on the stirring hot plate. The melt was allowed to cool. Following, the melt was crushed and ground to a fine powder in mortar and pestle. The powdered mix was used as a starting material in this Example and in Examples 2 to 5 hereafter.

A ten percent sodium bicarbonate (10% $NaHCO_3$) electrolytic solution (40 grams) containing an ammonium salt of sulphated dodecylphenoxy poly-(ethyleneoxy) ethanol as an emulsifier was placed in the cell. Powdered melt (4 grams) prepared as previously described was added. The cell was heated in the water bath by the stirring hot plate to a temperature of 90° to 95° C. As the powdered mixture melted, it was immediately emulsified. After the mixture was completely emulsified, power was applied at a constant current level of 100 milliamperes for 130 minutes. The cell voltage was monitored throughout the run. During the run, any organic compounds leaving the cell in the gaseous phase were collected in the perchloroethylene scrubber.

After the run was completed, the organic phase was separated from the aqueous, and it was analyzed to determine the product composition. Based on an accuracy range of ±5 percent, the conversion of pentachloropyridine was measured at 33.1 percent and the yields to symmetrical tetrachloropyridine and trichloropyridine were measured at 73.2 and 14.8 percent, respectively. The calculated current efficiency was 63.2 percent.

EXAMPLE 2

The procedure of Example 1 was repeated utilizing 12 percent potassium biphosphate ($K_2HPO_4$) as the electrolyte. The reaction was run for 240 minutes. The anode was replaced with an anode made out of magnetite. Using the accuracy range of Example 1, the conversion of pentachloropyridine was measured to be 41.3 percent. The yields to tetrachloropyridine and trichloropyridine were calculated to be 101.4 and 3.6 percent, respectively. The calculted value of the current efficiency was 41.4 percent.

EXAMPLE 3

The procedure of Example 2 was repeated except for the fact that the reaction was run for 160 minutes at a constant current of 150 milliamperes. Based on the aforementioned accuracy range, the conversion of pentachloropyridine was measured to be 44.7 percent. The yields to tetrachloropyridine and trichloropyridine were measured to be 96.3 and 3.8 percent, respectively. The calculated value of the current efficiency was 46.3 percent.

EXAMPLE 4

The procedure of Example 3 was repeated using a 12 percent sodium biphosphate ($Na_2HPO_4$) aqueous eletrolyte and ten (10) grams of pentachloropyridine/symmetrical tetrachloropyridine mix for an electrolyte to organic ratio of 4 to 1. The reaction was allowed to run for 90 minutes at a constant current of 150 milliamperes. Only 1.05 percent of the pentachloropyridine was converted.

EXAMPLE 5

The procedure of Example 4 was repeated by utilizing an electrolyte to organic ratio of 12 to 1. The conversion of pentachloropyridine was calculated to be 16.9 percent.

EXAMPLE 6

A flow-through electrochemical laboratory cell was constructed that included a cell and a mixing tank. The cell was a six inch by six inch flat, parallel-plate flow-through cell having a ⅛ of an inch material known by the trademark "Teflon" providing a gasket/spacer between the two electrodes. The mixing bath and the cell were heated in a ethylene-glycol bath to 95° C. A pH controller was provided to control the pH of the electrolyte in the cell. The flow-through cell was fitted with ruthenium oxide ($RuO_2$)-coated titanium (Ti) anode and a silver-sheet cathode.

A mixture containing pentachloropyridine (75 grams), symmetrical tetrachloropyridine (75 grams), ten percent (10%) brine (1,050 grams), and ammonium sulphate dodecylphenoxy poly-(ethyleneoxy) ethanol (2 grams) emmulsifier was added to the mixing tank, heated to 95° C. and stirred to form the emulsion prior to starting the run. Following, the emulsion was continuously pumped through the preheated cell at an approximate rate of two gallons per minute (2 gpm). The pH was constantly monitored and controlled by the addition of 1M sodium hydroxide (1M NaOH). The reaction was carried out for four hours. At the end of the run, a two-liter container of heated perchloroethylene was passed through the cell and added to the mixing tank. The chloropyridine compounds were dissolved in the solvent, extracted and analyzed by gas chromotography. Condensers were employed in the mixing tank and in the solvent container to minimize losses due to evaporation.

During the reaction, the current density was maintained constant at 0.25 Amps/$In^2$ and the cell voltage ranged from 2.81 to 4.03 Volts. At the end of the reaction the pentachloropyridine conversion was measured to be 17.4 percent. The product contained 4.51 weight percent trichloropyridines. The current efficiency was measured to be 3.2 percent. The amount of sodium hydroxide used to control the pH was 0.31 moles.

EXAMPLE 7

The procedure of Example 6 was repeated except for the fact that the current was pulsed on and off during the operation. More particularly, the current was turned on and maintained at 0.25 Amps/$In^2$ for sixty (60) seconds and then it was turned off for fifteen (15) seconds. The cycle was repeated for five hours, four hours being on the "on" mode and one hour being on the "off" mode. The cell voltage during the operation ranged from 2.27 to 2.61 Volts. The pentachloropyridine conversion was measudred to be 53.8 percent. The product contained 2.51 weight percent trichloropyridines. The current efficiency was 33.66 percent, a value significantly higher than the value of the current efficiency observed in Example 6.

EXAMPLE 8

An emulsion eletrolyte feed containing pentachloropyridine (75 grams), symmetrical tetrachloropyridine (75 grams), a zincate eletrolyte (1,050 grams), and ammonium sulphate dodecylphenoxy poly-(ethyleneoxy) ethanol emulsifier (2 grams) was added to the cell described in Example 6. The mixture was initially added to the mixing tank, heated to 95° C., and stirred to form an emulsion prior to starting the reaction. The emulsion then was continuously pumped through the preheated cell at a rate of six gallons per minute (6 gpm) for 2.5 hours. The zincate electrolyte contained 15 grams per liter Zinc and 150 grams per liter sodium hydroxide (NaOH). During the operation, the current was pulsed on and off. In the "on" mode, the current density was maintained constant at 0.5 Amps/$In^2$ for sixty (60) seconds. In the "off" mode, no current was passed through the cell for fifteen (15) seconds. The voltage of the cell ranged from 2.7 to 5.2 Volts. The conversion of pentachloropyridine was 54 percent. The product contained 8.08 weight percent of trichloropyridines. The current efficiency was measured to be 21 percent.

Although the invention is described with respect to specific embodiments and modifications, the details hereof are not to be construed as limitations except to the extent indicated in the following claims.

What is claimed is:

1. A process for making a symmetrical tetrahalopyridine from a pentahalopyridine in an electrolytic cell having an anode and a cathode, in the presence of an electrolyte, comprising the steps of:
    forming an organic solvent free emulsion of the pentahalopyridine and the tetrahalopyridine; and
    applying an electric current across the electrolytic cell to electrolyze the emulsion.

2. A process according to claim 1 further including the step of obtaining an organic phase and an aqueous phase.

3. A process according to claim 2 further including the step of separating the organic phase from the aqueous phase.

4. A process according to claim 1 further including the step of separating the symmetrical tetrahalopyridine from the pentahalopyridine.

5. A process according to claim 1 further including the step of maintaining the composition of the emulsion so that the emulsion remains in the liquid phase.

6. A process according to claim 1 further including the step of maintaining the temperature of the emulsion so that the emulsion remains in the liquid phase.

7. A process according to claim 1 wherein the cathode is made of copper.

8. A process according to claim 1 wherein the cathode is made of silver.

9. A process according to claim 1 wherein the anode is a titanium anode coated with ruthenium oxide.

10. A process according to claim 1 wherein the weight ratio of the electrolyte to the pentahalopyridine/tetrahalopyridine mixture is between 4 and 8.

11. A process according to claim 1 wherein the pH of the reaction is maintained between 6.5 and 9.

12. A process according to claim 1 wherein the electrolyte is an aqueous electrolyte.

13. A process according to claim 12 wherein the aqueous electrolyte is a salt that is not a strong base.

14. A process according to claim 12 wherein the aqueous electrolyte is a neutral salt.

15. A process according to claim 12 wherein the aqueous electrolyte is a zincate.

16. A process according to claim 15 wherein the zincate is a sodium zincate.

17. A process according to claim 1 wherein the emulsion-forming step includes the step of adding an emulsifier.

18. A process according to claim 1 further including the step of pulsating the current across the electrolytic cell.

19. A process according to claim 18 further including the step of desorbing the symmetrical tetrahalopyridine product from an electrode of the cell.

20. A process according to claim 18 wherein the step of pulsating the current includes the step of maintaining a first current density for a first time period followed by lowering the current density and maintaining the lowered current density for a second time period.

21. A process according to claim 20 wherein the magnitude of the lowered current density is zero.

22. A process according to claim 1 wherein the pentahalopyridine is pentachloropyridine and the symmetrical tetrahalopyridine is symmetrical tetrachloropyridine.

23. A process according to claim 22 wherein the temperature of the emulsion is maintained between 85° C. and 90° C.

24. A process according to claim 22 wherein the electric voltage across the cell is maintained between 2 and 3 volts.

25. A process according to claim 22 wherein the current density of the cell is maintained between 0.4 and 0.6 amperes per square inch.

* * * * *